United States Patent

Musinski

[11] Patent Number: 5,628,312
[45] Date of Patent: May 13, 1997

[54] APPARATUS FOR MEASURING SULFIDES WITHIN A PERIODONTAL POCKET

[75] Inventor: Donald L. Musinski, Seline, Mich.

[73] Assignee: Diamond General Development Corporation, Ann Arbor, Mich.

[21] Appl. No.: 489,657

[22] Filed: Jun. 12, 1995

[51] Int. Cl.$^6$ .................................................... A61B 5/00
[52] U.S. Cl. ............................................ 128/635; 128/734
[58] Field of Search .................... 433/72, 56; 128/635, 128/639, 642, 637, 734, 632

[56] References Cited

U.S. PATENT DOCUMENTS

| | | | |
|---|---|---|---|
| 5,131,844 | 7/1992 | Marinaccio et al. | 433/72 |
| 5,144,753 | 9/1992 | Murphy | 433/72 |
| 5,211,556 | 5/1993 | Kobayashi et al. | 433/72 |
| 5,275,161 | 1/1994 | Graves et al. | 128/635 |
| 5,318,442 | 6/1994 | Jeffcoat et al. | 433/72 |

FOREIGN PATENT DOCUMENTS

| | | | |
|---|---|---|---|
| 0384550 | 8/1990 | European Pat. Off. | 433/72 |
| 0274169 | 12/1989 | Germany | 433/72 |
| 8605382 | 9/1986 | United Kingdom | 433/72 |

*Primary Examiner*—Cary E. O'Connor
*Attorney, Agent, or Firm*—Gifford, Krass, Groh, Sprinkle, Patmore, Anderson & Citkowski, P.C.

[57] ABSTRACT

A probe for diagnosing periodontal disease includes a sulfide responsive measuring electrode and a reference electrode joined by a salt bridge. The reference electrode is maintained in a saturated salt environment. The probe may include a sound generation for providing an auditory indication of sulfide concentration.

15 Claims, 2 Drawing Sheets

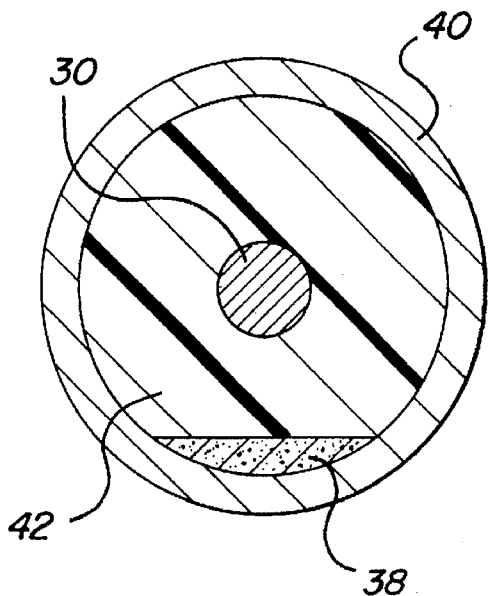
FIG-3
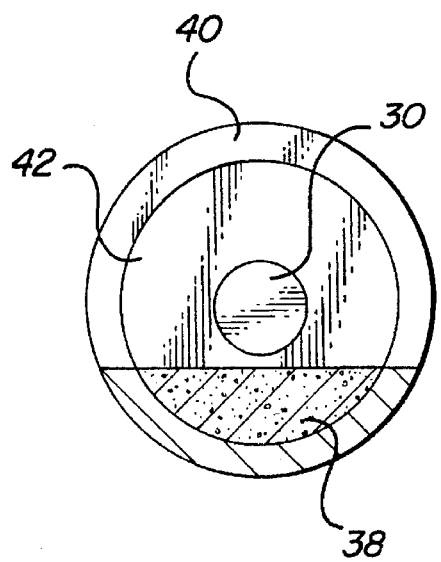
FIG-4
FIG-5
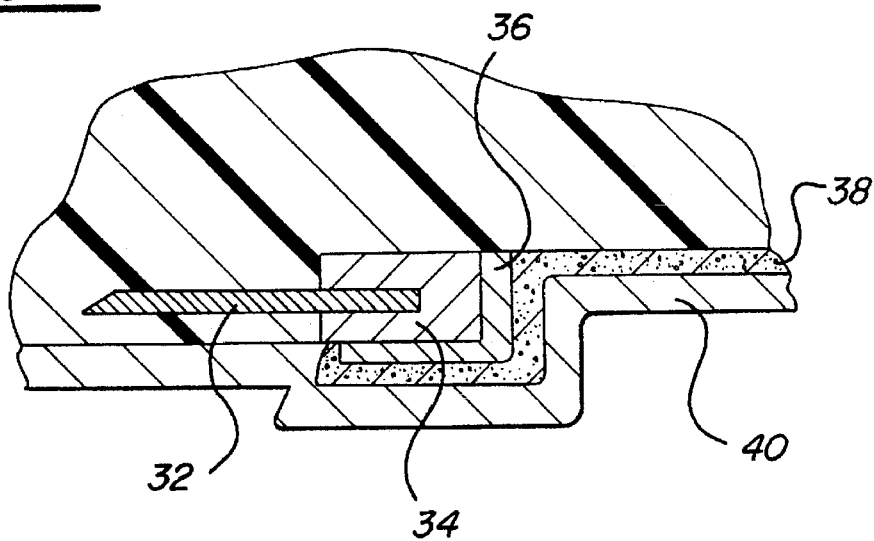

0
APPARATUS FOR MEASURING SULFIDES WITHIN A PERIODONTAL POCKET

FIELD OF THE INVENTION

This invention generally relates to the field of detecting gingivitis and periodontal disease and, more particularly, to an improved apparatus for measuring the concentration of sulfides within a periodontal pocket to determine the presence and extent of gingivitis and periodontal disease.

DESCRIPTION OF THE RELEVANT PRIOR ART

Gingivitis and periodontal diseases are, broadly speaking, diseases which cause inflammation of the gum area surrounding a tooth. They are thought to be caused by the activity of Gram-negative anaerobic organisms. Early symptoms include redness of the gingival margin surrounding the tooth, slight edema or slight retractability of this margin, and slight or delayed bleeding on probing of the margin. If left unchecked, gingivitis and periodontal disease may cause further and severe retraction of the gingival margin, continuous and/or spontaneous bleeding, and even, eventual loss of the tooth due to the erosion of the supporting and investing structures surrounding the tooth, including the gums, cementum, periodontal membranes and alveolar bone, even though the tooth itself, may be perfectly healthy. It is thought that, in the United States each year, more teeth are lost to gingivitis and periodontal disease than to disease and decay within the tooth, itself.

Typically, the presence of gingivitis and periodontal disease enlarges the periodontal pocket or gingival sulcus of the affected tooth. The gingival sulci are the spaces or pockets between the gingival tissue (gums) and the teeth. Many experts in the field are of the belief that there is a correlation between the depth of a periodontal pocket and the severity of the disease. The depth of the periodontal pocket is usually measured from the margin or top of the gum to the epithelial attachment, the point where the gum attaches to the tooth. It is measured with a mechanical probe. However, other experts doubt the reliability of this correlation since the gingival margins of some patients may exhibit fairly deep pockets, and yet the patients have little or no active periodontal disease within said pockets. In some cases, disease may have been present in the past, but the organisms which cause the disease may no longer be present,or if present, active in the pocket.

From a treatment standpoint, it is important to know whether active periodontal disease is occurring within a periodontal pocket, and, if so, how severe the disease is. Hence, because even deep periodontal pockets do not necessarily correlate with the presence of active periodontal disease, merely measuring the depth of the pocket does not necessarily provide an accurate indicator of the necessity of treatment. Clearly, it would be desirable to find a more accurate means of determining the presence and extent of active periodontal disease.

It is known that the presence of active disease agents within the periodontal pocket results in measurable concentrations of hydrogen sulfide gas within said pocket. According to an article authored by M. C. Solis-Gaffar, K. N. Rustogi, and A. Gaffar, appearing in the *Journal of Periodontology*, October 1980, pages 603–606, there is a measurable relationship between gingival health, crevicular fluid flow and the production of hydrogen sulfide from the crevicular fluid. Furthermore, these authors observed a positive, moderate correlation between the degree of observed inflammation and the $H_2S$ generating potential of the gingival crevicular fluid. An even stronger correlation was found between the sulfide gases generated in the gingival crevicular fluid (GCF) and the volume of GCF within the pocket. According to Solis-Gaffar, et al., hydrogen sulfide concentration of around 8 nanograms of sulfur per 10 milliliters of GCF are typical of healthy gingiva, whereas concentration of above 40 are characteristic of severe gingivitis.

The method used by Solis-Gaffar, et al. for determining the hydrogen sulfide generating potential of gingival crevicular fluid involved a chromatographic method; sterile filter paper strips were inserted into the crevice to collect the GCF. The analytic method disclosed is complicated, involving a three-day incubation of the strips with an appropriate amino-acid, and subsequent analysis with gas chromatography and a flame photometric detection system. Obviously, while useful for experimental purposes, the method disclosed in the Solis-Gaffar, et al. paper is not practical in a clinical setting. Other researchers have attempted to detect the presence of hydrogen sulfide by placing filter paper strips impregnated with lead acetate between the teeth and gums of patients suspected to be afflicted with periodontal disease (See A. A. Rizzo *Periodontics*, 5:233, 1967; and A. Horowitz and L. E. Fole, *Periodontal Abstracts*, 20:59, 1972.) Obviously, such methods are undesirable due to the known toxicity of lead. Additionally, such methods detect only the presence, not the concentration, of the sulfide gases and sulfide ions and particles in the sulcus fluid. Thus, with the above methods, quantitative measurements of the progress of periodontal disease cannot be made.

Other methods have been suggested for determining the presence of periodontal disease by either measuring the presence of certain components within the saliva or by probing the pocket with an electrochemical probe. For example, U.S. Pat. No. 4,334,540 to Preti broadly teaches a method for the detection of pyridines in mouth saliva. The reference teaches collecting saliva samples, incubating the samples, and collecting the volatiles from the saliva from the head space above the saliva. Again, this is an indirect method for making a gross determination of whether a patient has or is developing periodontal disease. U.S. Pat. No. 4,713,164 to Krietemeier discloses a method for analyzing malodors in the breath by means of a hand-held electrochemical detection means into which a sample gas stream is directed by blowing into the interior of the device. However, the reference does not teach anything about quantifying the presence or progression of periodontal disease, and does not teach how to make a hydrogen sulfide measurement around a specific tooth site. Also, it has been suggested by G. R. Mettraux, et al, *Journal of Periodontology*, 55:516–521 (1983) that an electrochemical sensor may be used to measure the concentration of oxygen in the sulcus of a tooth. Mettraux, et al., employ a $pO_2$ electrode which is inserted into the periodontal pocket. In this manner, the fluid in the periodontal pocket is measured to determine whether the subgingival environment is anaerobic or aerobic in nature. Finally, in Canadian Patent No. 1,279,370, an electro-chemical sensor is inserted into the sulcus of the tooth to polarographically determine the ratio of at least two gases selected from the group consisting of oxygen, ammonia, hydrogen, methane, carbon dioxide and hydrogen sulfide in the crevicular fluid. The ratio measurements are correlated with known parameters to indicate the nature and presence or progression of periodontal disease.

U.S. Pat. No. 5,275,161 discloses a method and apparatus for electro-chemically detecting and quantifying sulfide levels in gingival sulci. The method employs a probe which is inserted into the sulcus and which includes miniature measuring and reference electrodes. The potential developed between the electrodes is indicative of sulfide concentration and hence of disease condition. The method of the '161 patent is very accurate; however, it has been found that, in some instances, the sulfide can poison the reference electrode surface and lead to inaccurate results. The problem of sulfide poisoning is particularly severe when high sulfide concentrations are present and/or when a repetitive series of measurements are made. In electro-chemical systems of the type which include a measuring and reference electrode, the potential between the electrodes will depend on the ionic environment of each electrode. In sulfide measuring systems such as those of the '161 patent, it has been found that the measured potential will depend upon the chloride environment of the reference electrode. This effect is particularly significant when the two electrodes are physically separated, since the chloride environment of the reference electrode may vary from that of the measuring electrode in an unpredictable manner. The problem is complicated even further when a series of measurements are made on a given patient; because, in such instances, the probe is typically rinsed between readings, and rinsing can change the ionic environment of the electrodes. Therefore, it will be appreciated that there is a need for an electro-chemical measuring system which is stable in use, and through repeated rinsings.

Accordingly, it will be appreciated that there is a need for an electrode system for measuring periodontal sulfide concentrations which is resistant to sulfide poisoning. It is further desirable that any such system be accurate, stable, self-contained, capable of being used for a repetitive series of measurements, and low enough in cost that patient contacting portions thereof can be disposed after use.

Yet another problem encountered with prior art systems for measuring periodontal disease is resultant from the fact that positioning of the measuring probe within the patient's mouth requires a fair degree of manual dexterity and attention. The confines of the sulcus are relatively small, and it is frequently necessary to move the probe about within the sulcus in order to obtain an accurate reading of the extent of periodontal disease; as a result, the practitioner cannot easily monitor a visual display. Hence, inaccurate, or incomplete, measurements may be made. Therefore, there is a need for a system which provides an indication, in real time, of periodontal sulfide concentrations, and which does not necessitate visual reading of a display.

In accord with the present invention, there is provided a system for assessing the presence and extent of periodontal disease. The system includes a probe which is insensitive to poisoning by sulfide compounds. Additionally, the system allows a practitioner to non-visually monitor sulfide level concentrations, in real time, while manipulating the probe within the periodontal sulcus. These and other advantages of the present invention will be readily apparent from the drawings, discussion and description which follow.

BRIEF DESCRIPTION OF THE INVENTION

There is disclosed herein a probe for diagnosing the presence and extent of disease in a periodontal pocket containing sulcal fluid, by measuring the concentration of sulfides in said fluid. The probe comprises a housing having a first end which defines a tip configured to probe a periodontal pocket. A sulfide responsive measuring electrode is supported by the housing with a surface portion thereof disposed in the tip so as to establish fluid communication with the sulcal fluid when the tip is disposed in the pocket.

The probe further includes a reference electrode supported by the housing at a location which will not directly contact the sulcal fluid when the tip is disposed in the pocket. The reference electrode has a surface portion thereof disposed in a body of a salt. The probe also includes a salt bridge material which is disposed so as to establish a conductive path between the body of salt and measuring electrode when the tip is disposed in the sulcal fluid. The probe further includes a first electrical lead in communication with the measuring electrode and a second electrical lead in electrical communication with the reference electrode. The probe is operative, when immersed in the sulcal fluid, to generate an electrical potential between the measuring electrode and the reference electrode which is proportioned to a concentration of sulfide in the sulcal fluid. In further embodiments, the probe includes a hydration layer supported by the housing between the measuring electrode and reference electrode. The hydration layer may comprise a polymeric matrix having a salt residue disposed in the pores. In one particular embodiment, the polymeric material comprises cellulose acetate, and the pores contain an aqueous phase comprising a salt solution.

In particular embodiments, the reference electrode is disposed in a pellet of a salt such as potassium chloride, and a major portion of the pellet of salt is covered with a moisture impervious material so as to leave only a small opening for fluid access to the salt pellet. The salt bridge material may, in one instance, comprise an organic matrix having particles of a salt dispersed therein.

In yet other embodiments, the probe includes an auditory signal generator associated therewith for sensing the potential generated between the measuring electrode and reference electrode, and providing an auditory signal corresponding thereto.

BRIEF DESCRIPTION OF THE DRAWINGS

FIG. 3 is a cross-sectional view of the probe of FIG. 2 taken along line 3—3;

FIG. 4 is an end view of the probe of FIG. 2;

FIG. 5 is an enlarged, cross-sectional view of a portion of the probe of FIG. 2 better illustrating the reference electrode and salt block.

DETAILED DESCRIPTION OF THE INVENTION

Figure 1:
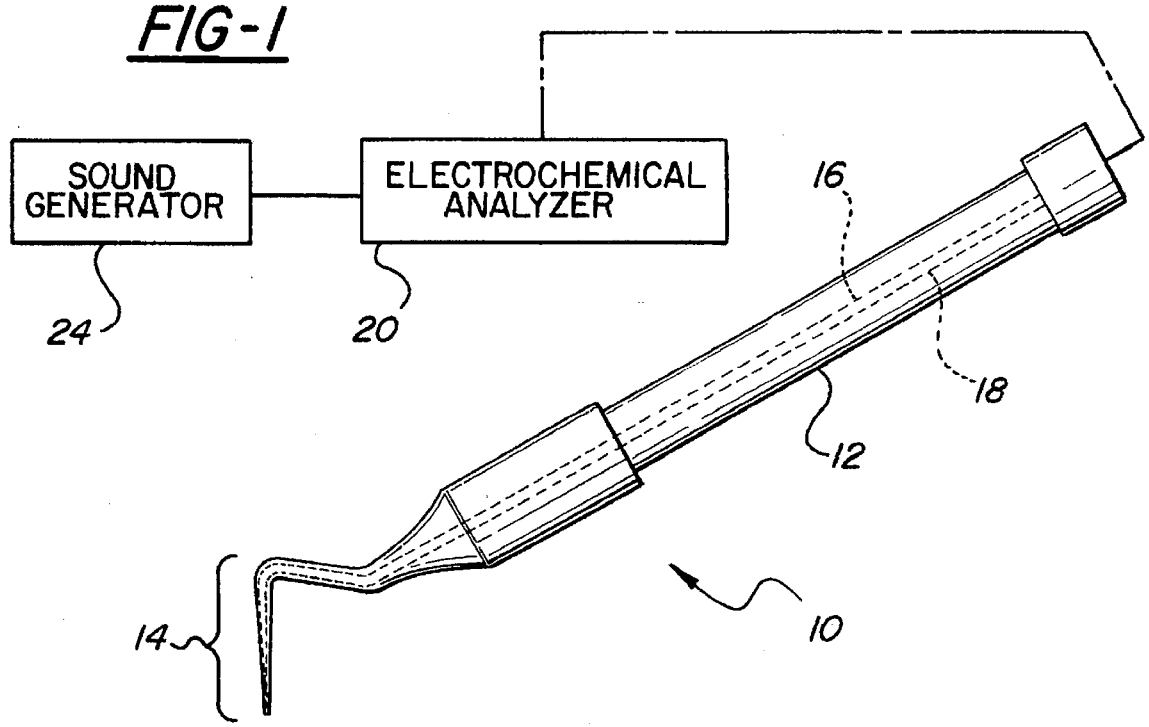
FIG. 1 is a depiction of a probe structured in accord with the present invention.

The present invention is directed to a periodontal probe for measuring the sulfide concentration of sulcal fluid. The probe of the present invention is resistant to sulfide poisoning, and is stable in operation through repeated rinsings. FIG. 1 depicts a typical probe 10 structured in accord with the principles of the present invention. The probe 10 includes a housing 12 having a length and a diameter configured to be easily handled by a practitioner and manipulated in the mouth of a patient. A portion of the housing 14 is configured to define a relatively small diameter tip configured to enter a patient's sulcal pockets.

As will be described in greater detail hereinbelow, the probe 10 includes a sulfide responsive measuring electrode, and a reference electrode. These electrodes each connected to a respective, electrically conductive lead 16, 18 shown herein in phantom outline. The leads 16, 18 are in electrical communication with an electro-chemical analyzer 20 which may optionally include a sound generator 24 in communication therewith.

In operation, the probe is disposed so that the tip portion thereof is immersed in the patient's sulcal fluid so that the measuring electrode contacts the fluid. The reference electrode is also in electrical communication with the sulcal fluid, via a salt bridge, as will be described in greater detail hereinbelow; although, the reference electrode may not be actually immersed in the sulcal fluid. An electrical potential is developed between the measuring electrode and the reference electrode, and this potential is proportional to the sulfide concentration in the sulcal fluid. The electro-chemical analyzer 20 is operative to sense the potential between the electrodes and to provide a display which is directly indicative of, or correlatable with, sulfide concentration. Since, in both instances, it is difficult for a practitioner to observe a visual display while properly positioning the probe in the sulcal pocket, a sound generator 24 may be utilized in combination with the electro-chemical analyzer 20. The sound generator 24 produces an audible signal which is indicative of the potential generated between the electrodes. The sound generator may be operative to provide a signal having a pitch or volume which varies as a function of the measured potential; or, the sound generator 24 may be operative in a threshold manner to provide a signal only if a preselected potential is achieved.

It has been found that sulfide concentration in a sulcal pocket may have a spatial variation. Generally, it is most desirable to measure the highest sulfide concentration. The use of an audible signal generator simplifies probing of the pocket by providing a direct, non-visual signal indicative of the magnitude of the potential. In a further refinement of this embodiment, the electro-chemical analyzer may be operative to store the highest potential measured so as to permit later reference thereto.

Figure 2:
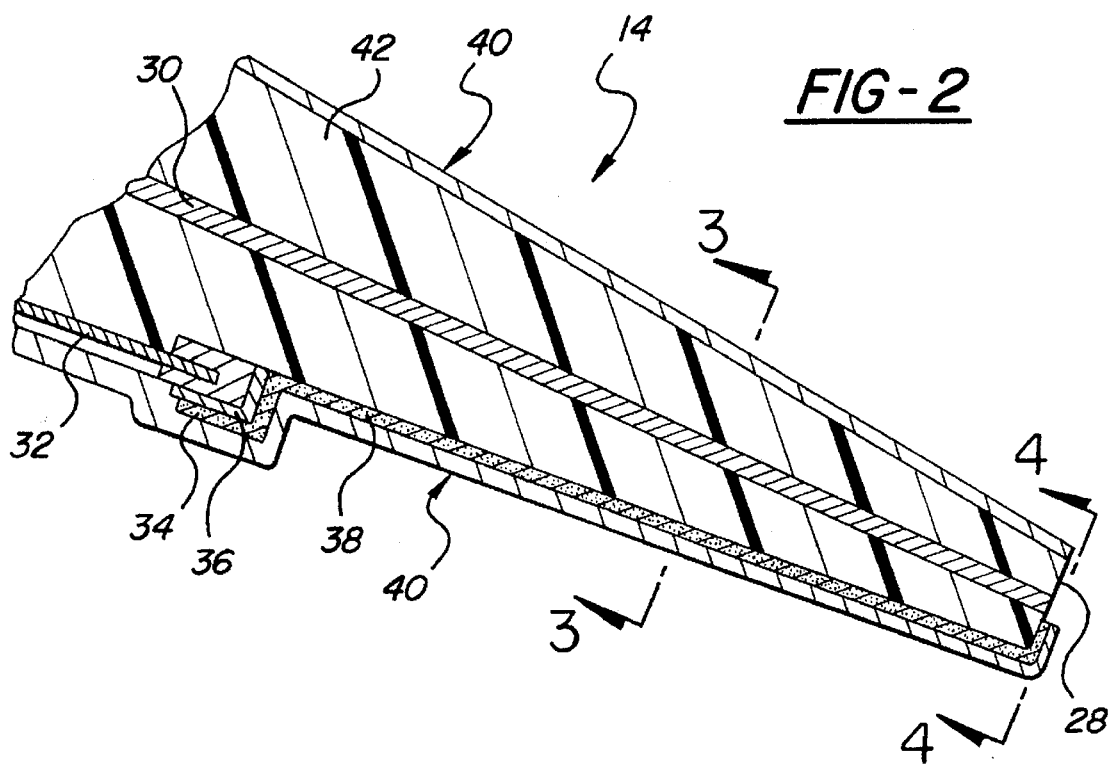
FIG. 2 is an enlarged, cross-sectional view of a portion of the probe of FIG. 1.

Referring now to FIG. 2, there is shown an enlarged, cross-sectional view of a portion 14 of the probe 10, including the tip portion at the first end 28 thereof which, in the operation of the probe, is placed in the periodontal pocket.

As illustrated, the portion of the housing shown in FIG. 2 is configured as a generally tapered member 42 fabricated from a body of an electrically insulating material, such as polymer. The housing may comprise a body of solid material onto which the various components of the tip are attached, or it may be made from a curable resin. A sulfide responsive measuring electrode 30 is disposed therein. This electrode 30 is most preferably fabricated from a material which undergoes an electro-chemical reaction with the sulfide ion. One particularly preferred material comprises silver, and accordingly, the electrode 30 may be simply comprised of a fine silver wire. In other instances, the electrode may comprise a wire, such as a stainless steel wire, coated with silver. Other metals reactive with sulfide may be similarly employed, for example antimony. The measuring electrode 30 is disposed so that a surface portion thereof, for example portion 30' as shown in FIG. 4, is exposed at the tip 28 end of the probe for contact with sulcal fluid.

As is known in the art, a reference electrode, disposed in an electro-chemical relationship with the measuring electrode 30 must be employed in order to provide a potential indicative of a sulfide ion concentration. In the illustrated embodiment, a reference electrode 32 is disposed in the probe. One particularly preferred reference electrode comprises a silver/silver chloride electrode, typically provided by disposing a chloride coating on a silver wire. In some instances, the chloride coating will be disposed to cover a substantial length of the wire, and in other instances, the wire will be insulated along substantially all of its length, and will have a body of silver chloride disposed so as to cover a free end of the wire. All such configurations may be employed in the practice of the present invention.

It has been found that the operating voltage of the reference electrode is dependent upon the logarithm of the chloride ion concentration to which it is exposed. And in the use of electrode systems of the prior art, it has been found that the chloride ion concentration in the vicinity of the reference electrode can vary over a wide range of values and such variation is further increased when the electrode is rinsed between uses. Variations of chloride concentration lead to fluctuations in the reference voltage, and hence a variation in the final reading of sulfide ion concentration. In accord with the present invention, it has been found that the output of the reference electrode can be stabilized, if the electrode is disposed in a saturated chloride solution. Toward that end, the reference electrode 32 is disposed within a pellet of a salt, such as potassium chloride 34. As will be better seen in FIG. 5, the pellet of potassium chloride 34 is partially covered by the material of the housing 42, and preferably has a major portion of its free surface covered by a moisture impervious material 36, such as a layer of epoxy resin. The moisture impervious layer 36 covers most, but not all, of the pellet 34. When the probe is first prepared for use, it is immersed in a rinse/hydration solution. This solution enters the opening in the impervious layer 36 and moistens the salt comprising the pellet 34 so as to produce a saturated solution therein in the region of the reference electrode 32. The fact that the opening in the impervious layer 36 is relatively small limits entry of water and dissolution of the pellet 34 when the probe is subsequently rinsed.

It is necessary that the measuring electrode and reference electrode be in electrical communication if an accurate reading is to be obtained. As noted above, problems arise in prior art systems in which the reference electrode is disposed in the sulcal fluid during use, because of sulfide poisoning of the electrode. In accord with the present invention, the reference electrode is removed from contact with the sulcal fluid, and ionic conductivity between the reference electrode and the measuring electrode is established through a salt bridge. As illustrated in the Figures, a salt bridge 38 extends from the salt pellet 34 to the tip 28 of the probe. As is known in the art, a salt bridge material comprises a body having mobile ions contained therein for providing ionic conductivity therethrough. One particularly preferred salt bridge material for the practice of the present invention comprises an organic matrix defining an open lattice having a plurality of interconnected channels therethrough with an aqueous salt solution contained in the channels. One specific and preferred salt bridge material comprises an epoxy polymer matrix with potassium chloride contained therein.

it has been found, in accord with the present invention, that a salt bridge may be readily provided within the probe by disposing a layer 38 of an epoxy polymer having a salt dispersed therein, between the salt pellet 34 surrounding the reference electrode 32, and the region of the tip proximate the measuring electrode 30. Preferably, the salt bridge is prepared by coating a thin layer of curable epoxy resin and sprinkling potassium chloride salt onto the unhardened epoxy layer. The salt penetrates the layer, and the layer subsequently hardens. When the salt bridge layer is hydrated during the initial wash of the electrode, salt exposed on the surface of the bridge hydrates forming an electrically conductive surface layer. The salt embedded within the underlying matrix is leached from the matrix during successive washings so as to regenerate the conductive surface. While a variety of salts may be employed in the practice of the present invention, potassium chloride is particularly preferred because the mobility of the potassium ions and the chloride ions in solution is comparable, thereby avoiding space charge effects and the like. While epoxy resin is described as one preferred material for the fabrication of the salt bridge, it is to be understood that within the context of the present invention, the salt bridge may be fabricated from any matrix material, including organic as well as inorganic materials, which can contain salt crystals, which crystals are subsequently leached during hydration and operation of the bridge.

In accord with another feature of the present invention, there is provided a hydration layer 40 on the probe, in the region of the reference electrode, measuring electrode and salt bridge. The hydration layer comprises a smooth, open structured, over coated layer which assures the maintenance of hydrated conditions between the electrodes and salt bridge and allows for wider tolerances in the fabrication of the salt bridge. As illustrated in FIGS. 2–5, the hydration layer 40 comprises a layer overcoating the tip portion of the probe, and as such covers the salt bridge layer 38. One particular hydration layer is comprised of a porous cellulose acetate layer containing a salt residue lining the pores. The layer may be prepared by coating an emulsion comprising an organic phase, which is an organic cellulose acetate solution, and an aqueous phase which comprises an aqueous salt solution. Upon evaporation of the organic solvent, the water based phase is trapped within the cellulose acetate matrix. Subsequent evaporation of the water droplets opens small pores in the coating matrix and leaves a salt residue that assists in hydration of the coating during the initial wash/hydration step.

A number of different materials may be utilized for the hydration layer. As noted, one preferred material involves cellulose acetate, and it has been found that a hydration layer may be prepared from a 30% solution of cellulose acetate in acetone formed into an emulsion with up to 1% of an aqueous solution of 4M potassium chloride. Other embodiments of hydration layer may similarly be prepared from a variety of polymers such as cellulose acetate-butyrate, vinyls, and the like. In general, the polymer and solvent system should be chosen so as to allow for initial evaporation of the organic phase with the aqueous phase remaining, so as to provide the porous, salt containing matrix.

In use, the probe of the present invention is first rinsed with a wash/hydration solution so as to wet the hydration layer, salt bridge, and salt pellet. The wash/hydration solution may simply comprise water, or may comprise a dilute salt solution and may further include disinfectants, surfactants and the like. Either before, or after hydration, the probe is placed in electrical connection with a standard electrochemical analyzer such as a D. G. Electro-Chem analyzer (Model 1200) by means of a standard connector such as a mini coaxial connector cable, which is attached to the first and second leads of the probe. The mode switch of the analyzer is set down to a reference position and the selector control to the lower volt position (inactivating most other controls). The power supply switch of the analyzer is turned on and the probe tip may be placed in a sterile 0.5 molar NaCl solution. A base line reading may be taken which will usually vary between 30–100 mV+, reflecting the potential difference between the first and second electrodes in the probe, that is, the silver versus silver/silver chloride potential in the saline solution. If desired, the probe may then be dipped into a calibration solution including a known concentration of sulfide ion to verify operation thereof.

Once hydrated, the probe is ready for insertion into a periodontal pocket of a patient. The probe is inserted so that it comes into contact with the periodontal sulcal fluid contained therein. As noted above, the probe is configured so that the reference electrode does not directly contact the sulcal fluid in normal use. The electrolytes within the sulcal fluid will cause an electrical potential to develop between the electrodes, the magnitude of which corresponds to the concentration of sulfide in the fluid. Typically, a clearly, clinically-observable diseased or inflamed pocket should produce a readout on the analyzer in the 500–700 mV+ range. Responses in the range of 250–500 mV+ may indicate subclinical disease activity not readily diagnosable by conventional means. Readings below this level may be borderline. Readings below the borderline (i.e. 250 mV+) down to the base line (typically 30–100 mV+) generally indicate an absence of active disease.

After measurement of each pocket, the probe tip is immersed in a sterile rinse solution. As noted above, the particular configuration of the reference electrode prevents disintegration and depletion of the salt during the rinse steps.

While one particular configuration of probe has been illustrated, it will be appreciated that in accord with the principles disclosed herein, other configurations may be implemented. For example, the probe may be fabricated in an inverted embodiment wherein the housing may comprise a hollow, tapered cylindrical body which encloses the measuring electrode as well as the reference electrode, salt pellet, salt bridge and hydration layer. In another embodiment, the measuring electrode will comprise a cylindrical body which forms the tip itself as well as the electrode. In this particular embodiment, the reference electrode may be disposed upon an electrically insulating coating covering a portion of the body forming the reference electrode, and may be connected thereto by the salt bridge as previously noted. The reference electrode may be disposed in yet other configurations, provided that it is separated from the sulcal fluid by salt bridge material and provided that ionic conductivity between the reference electrode and measuring electrode is established.

In view of the foregoing, it will be appreciated that numerous other modifications and variations of the present invention may be implemented. The foregoing drawings, discussion and description are meant to be illustrative of particular embodiments of the invention and not meant to be limitations upon the practice thereof. It is the following claims, including all equivalents, which define the scope of the invention.

I claim:

1. A probe for diagnosing the presence and extent of disease in a periodontal pocket containing sulcal fluid, by measuring the concentration of sulfides in said fluid, said probe comprising:

a housing having a first end defining a tip configured to probe the periodontal pocket;

a sulfide-responsive, measuring electrode supported by said housing with a surface portion thereof disposed in said tip so as to establish fluid communication with said sulcal fluid when said tip is disposed in said pocket;

a reference electrode supported by said housing at a location which will not contact said sulcal fluid when the tip is disposed in the pocket, said reference electrode having a surface portion thereof disposed in a body of a salt;

a salt bridge material which is disposed so as to establish a conductive path between said body of salt and said measuring electrode when the tip is disposed in the sulcal fluid;

a first electrical lead in electrical communication with the measuring electrode;

a second electrical lead in electrical communication with the reference electrode;

said probe being operative, when immersed in said sulcal fluid, to generate an electrical potential between said measuring electrode and said reference electrode which is proportional to the concentration of sulfide in said sulcal fluid.

2. A probe as in claim 1, further including a hydration layer disposed in contact with said salt bridge material.

3. A probe as in claim 2, wherein said hydration layer comprises a porous organic polymer having a salt disposed within said pores.

4. A probe as in claim 3, wherein said organic polymer comprises cellulose acetate.

5. A probe as in claim 1, wherein said body of salt has a major portion of the surface thereof which is covered by a moisture impervious coating and a minor portion thereof which is free of said coating.

6. A probe as in claim 5, wherein said body of salt is a body of potassium chloride.

7. A probe as in claim 1, wherein said salt bridge material comprises an organic matrix having particles of a salt disposed therein.

8. A probe as in claim 7, wherein said organic matrix comprises a polymer.

9. A probe as in claim 8, wherein said polymer comprises an epoxy polymer.

10. A probe as in claim 7, wherein said salt comprises potassium chloride.

11. A probe as in claim 1, further including an auditory signal generator in electrical communication with said first and second electrical leads, said signal generator being operative to sense the potential generated between said measuring electrode and said reference electrode and to provide an auditory signal corresponding thereto.

12. A probe for diagnosing the presence and extent of disease in a periodontal pocket containing sulcal fluid, by measuring the concentration of sulfides in said fluid, said probe comprising:

a housing;

a tip configured to probe a periodontal pocket, said tip being disposed at a first end of said housing;

a sulfide-responsive, measuring electrode supported by said housing with a surface portion thereof disposed in said tip so as to establish fluid communication with said sulcal fluid when said tip is disposed in said pocket;

a reference electrode supported by said housing;

a body of salt bridge material disposed so as to establish ionic conductivity between the measuring electrode and the reference electrode and to prevent direct fluid contact of the reference electrode with the sulcal fluid;

a first electrical lead in electrical communication with said measuring electrode;

a second electrical lead in electrical communication with said reference electrode;

said probe being operative, when immersed in said sulcal fluid, to generate an electrical potential between said measuring electrode and said reference electrode which is proportional to the concentration of sulfide in said sulcal fluid.

13. A system for diagnosing the presence and extent of disease in a periodontal pocket containing sulcal fluid, said system including:

a sulfide responsive probe comprising: a housing having a tip configured to probe a periodontal pocket disposed at a first end thereof, a measuring electrode and a reference electrode, operative to establish an electrical potential therebetween when said tip is immersed in a sulfide containing fluid, said potential being proportional to the concentration of sulfide in said fluid; and an auditory signal generator in electrical communication with said probe, said signal generator being operative to sense the potential generated by said electrodes and provide an auditory signal corresponding thereto.

14. A system as in claim 13, wherein said signal generator is further operative to provide a visual display corresponding to said potential.

15. A system as in claim 13, wherein said signal generator is further operative to store data indicative of the highest potential sensed thereby.

* * * * *

UNITED STATES PATENT AND TRADEMARK OFFICE
CERTIFICATE OF CORRECTION

PATENT NO.   : 5,628,312  
DATED        : May 13, 1997  
INVENTOR(S)  : Donald L. Musinski et al.

Page 1 of 1

It is certified that error appears in the above-identified patent and that said Letters Patent is hereby corrected as shown below:

Title page,
Item [75], Inventor, should read as follows:
-- [75] Inventors: Donald L. Musinski, Seline; Bruce B. Graves, Ypsilanti, both of Mich. --.

Signed and Sealed this

Seventh Day of May, 2002

*Attest:*

*Attesting Officer*

JAMES E. ROGAN  
*Director of the United States Patent and Trademark Office*

UNITED STATES PATENT AND TRADEMARK OFFICE
CERTIFICATE OF CORRECTION

PATENT NO.    : 5,628,312
DATED         : May 13, 1997
INVENTOR(S)   : Donald L. Musinski et al.

It is certified that error appears in the above-identified patent and that said Letters Patent is hereby corrected as shown below:

<u>Title page,</u>
Item [75], Inventor, should read as follows:
-- [75] Inventors: Donald L. Musinski, Saline; Bruce B. Graves, Ypsilanti, both of Mich. --.

This certificate supersedes Certificate of Correction issued May 7, 2002.

Signed and Sealed this

Twelfth Day of November, 2002

*Attest:*

JAMES E. ROGAN
*Attesting Officer*        *Director of the United States Patent and Trademark Office*